United States Patent
Wada et al.

(10) Patent No.: US 8,395,015 B2
(45) Date of Patent: Mar. 12, 2013

(54) ABSORPTIVE ARTICLE

(75) Inventors: Ichiro Wada, Kagawa (JP); Miou Suzuki, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 595 days.

(21) Appl. No.: 12/597,306

(22) PCT Filed: Apr. 24, 2008

(86) PCT No.: PCT/JP2008/057973
§ 371 (c)(1),
(2), (4) Date: Oct. 23, 2009

(87) PCT Pub. No.: WO2008/136362
PCT Pub. Date: Nov. 13, 2008

(65) Prior Publication Data
US 2010/0069862 A1    Mar. 18, 2010

(30) Foreign Application Priority Data
Apr. 26, 2007    (JP) .................................. 2007-116650

(51) Int. Cl.
*A61F 13/15*    (2006.01)
*A61F 13/20*    (2006.01)

(52) U.S. Cl. ........ 604/361; 604/346; 604/347; 604/348; 604/354

(58) Field of Classification Search .......... 604/346–348, 604/354, 361
See application file for complete search history.

(56) References Cited

U.S. PATENT DOCUMENTS

| 2,947,415 | A | * | 8/1960 | Garth .......................... 206/364 |
| 4,993,555 | A | * | 2/1991 | Hemm .......................... 383/205 |
| 6,246,330 | B1 | * | 6/2001 | Nielsen .......................... 340/604 |
| 7,477,156 | B2 | * | 1/2009 | Long et al. ................. 340/573.5 |

FOREIGN PATENT DOCUMENTS

| JP | H03-39031 | 4/1991 |
| JP | H03-1135 | 7/1996 |
| JP | 2000-093448 | 4/2000 |
| JP | 2005-52563 | 3/2005 |

(Continued)

OTHER PUBLICATIONS

International Search Report from corresponding PCT application No. PCT/JP2008/057973, dated May 20, 2008, 2 pages.

(Continued)

*Primary Examiner* — Loan Thanh
*Assistant Examiner* — Aundria Hairell
(74) *Attorney, Agent, or Firm* — Brinks Hofer Gilson & Lione

(57) ABSTRACT

An absorptive article in which a terminal section of a sensor is less likely to be damaged in production, packaging, and transportation. An output terminal (115) of a sensor member (110) is placed at a side end of a front edge (180) of a urine pad (100). The side end of the front edge (180) is constructed only from a front face sheet (105) and a rear face sheet (106). The front face sheet (105) and the rear face sheet (106) are not joined together and are separably arranged. When the urine pad (100) is not in use, the output terminal (115) is covered by the front face sheet (105) and the rear face sheet (106). In use, the front face sheet (105) and the rear face sheet (106) are separated in the thickness direction and the output terminal (115) of the sensor member (110) is exposed.

4 Claims, 13 Drawing Sheets

FOREIGN PATENT DOCUMENTS

| | | |
|---|---|---|
| JP | 2005-102979 | 4/2005 |
| JP | 2007-044493 | 2/2007 |
| JP | 2007-044494 | 2/2007 |
| JP | 2009-006180 | 1/2009 |

OTHER PUBLICATIONS

Notice of Reasons for Rejection issued in corresponding Japanese Application No. 2007-116650, dated Mar. 27, 2012, 5 pages.

* cited by examiner

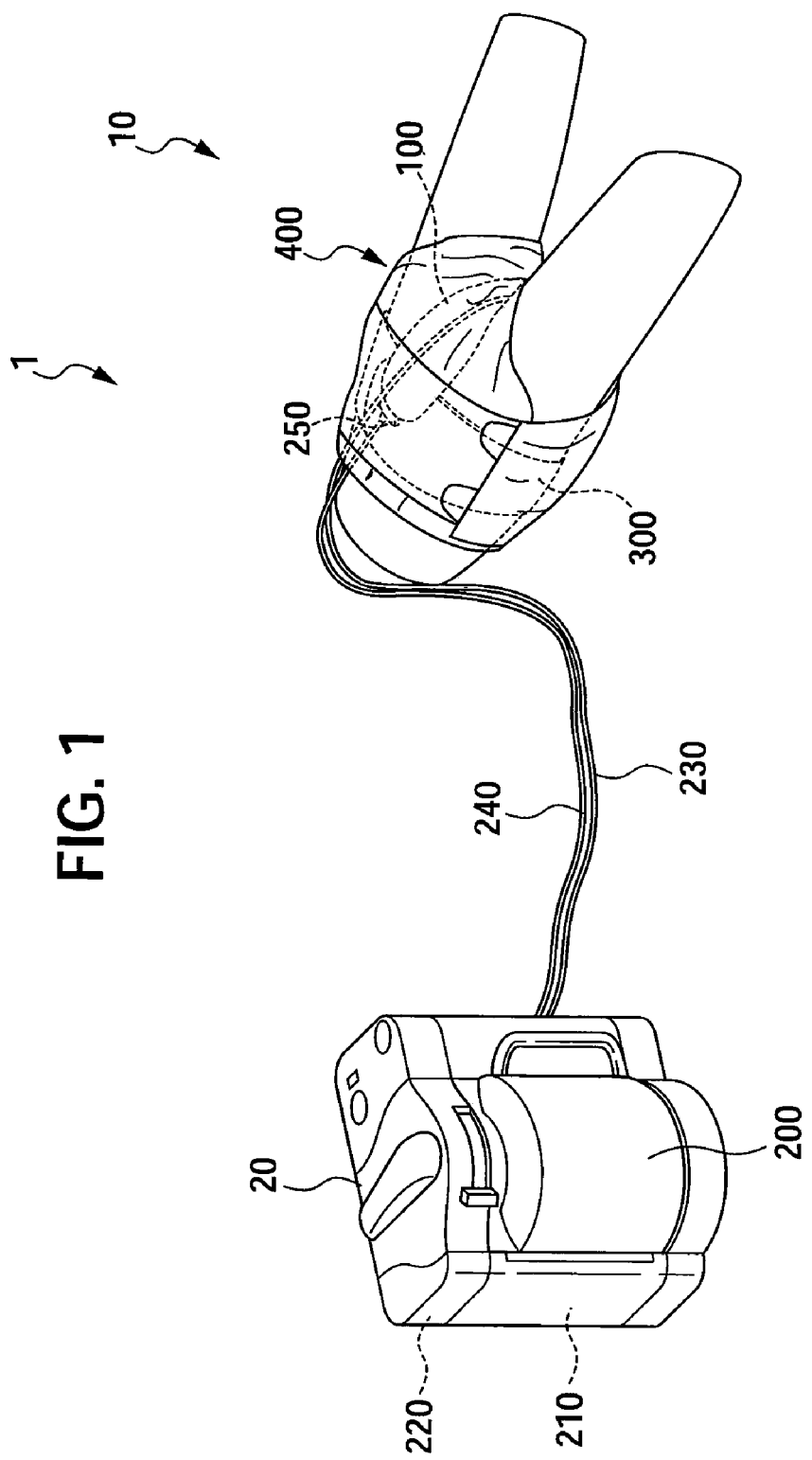

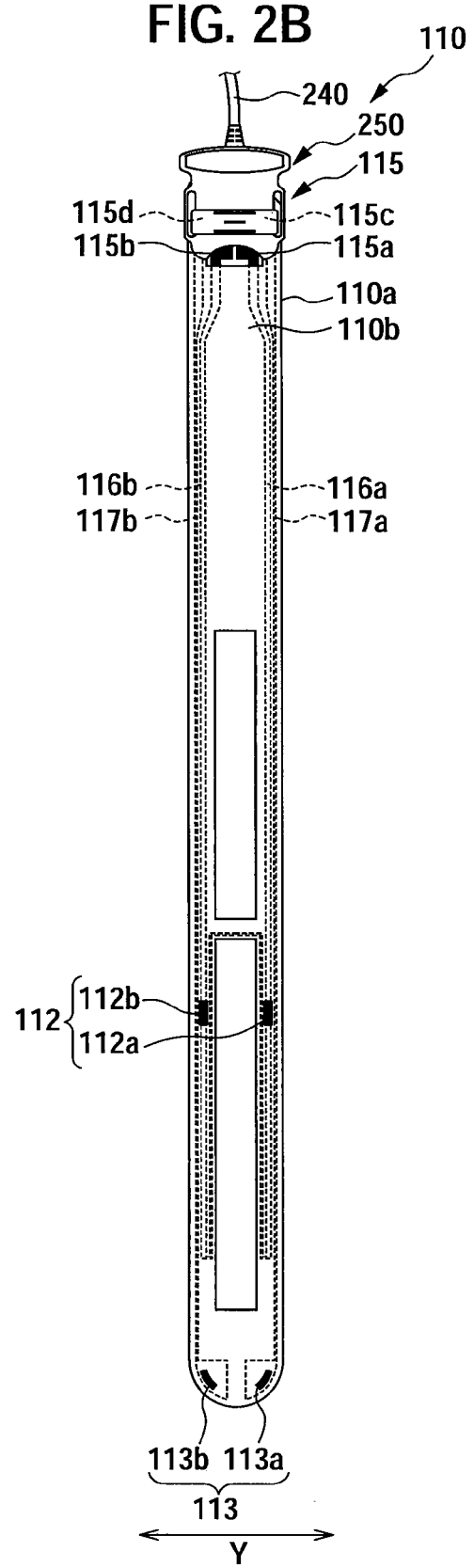

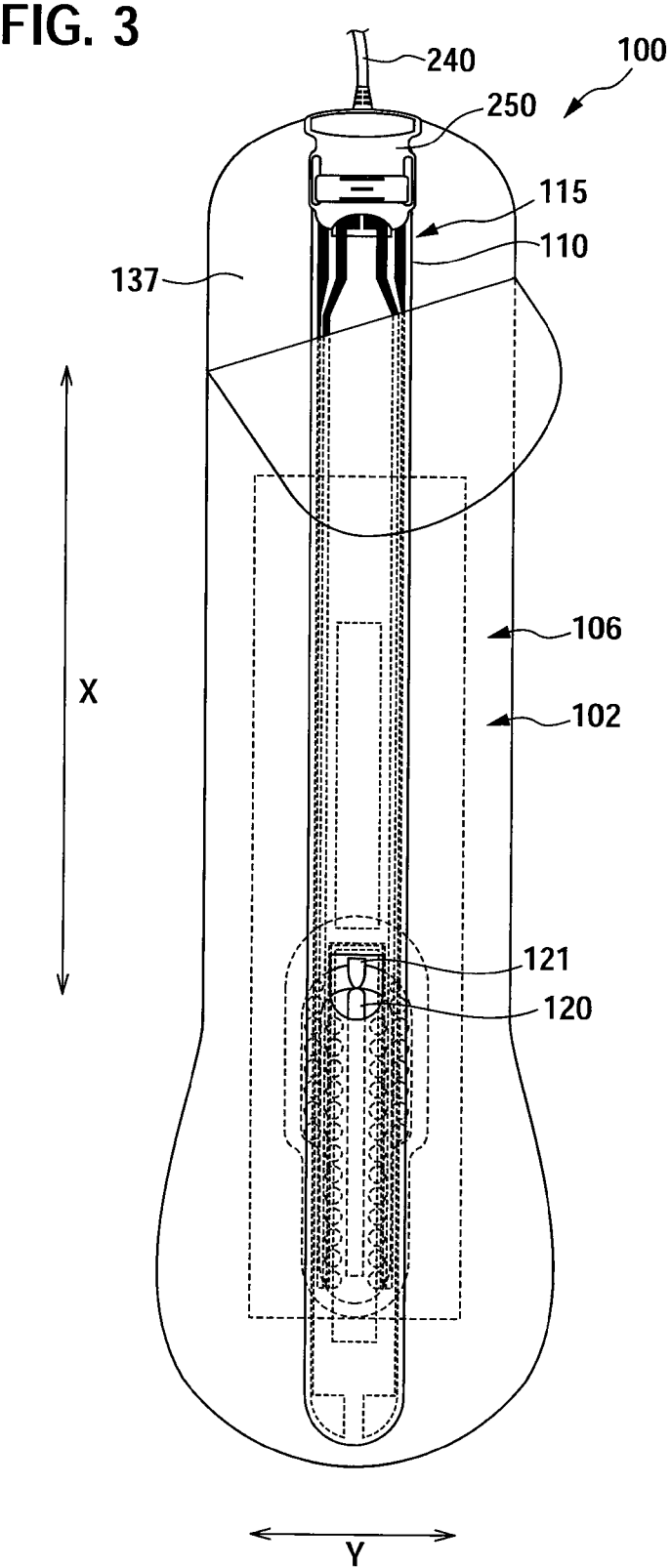

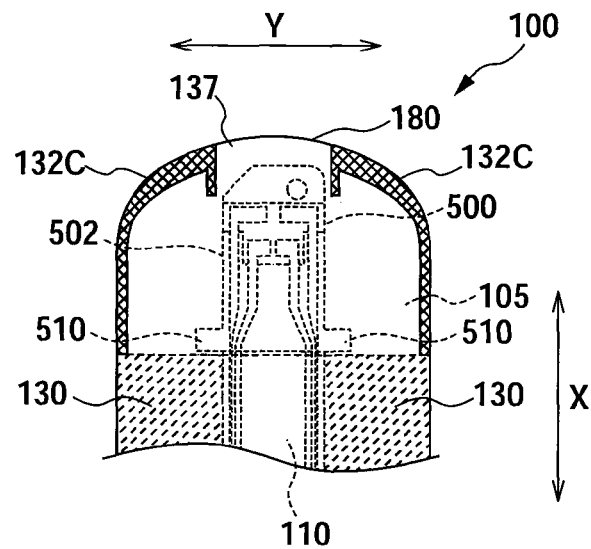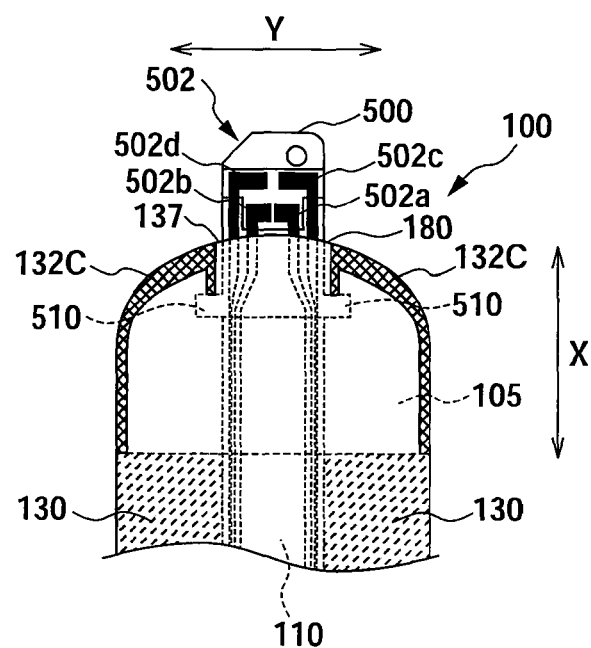

ABSORPTIVE ARTICLE

RELATED APPLICATIONS

This application is a 35 U.S.C. §371 national phase filing of International Patent Application No. PCT/JP2008/057973, filed on Apr. 24, 2008, to which priority is claimed under 35 U.S.C. §120 and through which priority is claimed under 35 U.S.C. §119 to Japanese patent application No. 2007-116650, filed Apr. 26, 2007.

TECHNICAL FIELD

The present invention relates to an absorbent article.

BACKGROUND ART

There is proposed disposing excretory substances as a main work of care for those who require care such as elderly people who keep to their bed and cannot stand on their own legs, an ill person, and the like. Although care such as disposing excretory substances is done in accordance with physical conditions of those who require care, an absorbent article such as a diaper has been known which disposes excretory substances in a case where those who require care cannot control their excretory substances or go to a bathroom during nighttime hours. The absorbent article such as a diaper holds excretory substances such as urine excreted so that the excretory substances are not leaked outside of the absorbent article.

A caretaker can use an absorbent article such as a diaper, which allows a caretaker to reduce the burden on care. However, in a case where excretory substances are retained for a long period of time, smell, germ, and the like are occurred from excretory substances held in the absorbent article, thereby exerting a harmful influence to those who require care. Furthermore, in a case where voluminous excretory substances are excreted because of, for example, pollakiuria, and are leaked from the absorbent article, a caretaker needs to replace the contaminated clothing, which situation increases the burden on care.

As for the foregoing, a care system has been proposed which is composed of a urine receiver, an aspirating tube connecting to the urine receiver, and aspirating configuration placed outside of the urine receiver (for example, Japanese Unexamined Patent Application, First Publication No. 2007-44494). According to the care system disclosed in Japanese Unexamined Patent Application, First Publication No. 2007-44494, the urine receiver receives excretory substances such as urine excreted from those who require care, and then the urine thus received by the urine receiver is aspirated outside of the urine receiver by the aspirating configuration. Based on the abovementioned configuration, excretory substances from those who require care are not leaked outside, and the excretory substances are not held in the urine receiver, whereby it can prevent the excretory substances from being contacted to the skin of those who require care for a long period of time. In addition, even in a case where voluminous excretory substances are excreted, the urine receiver can be applied to those who require care for a long period of time without replacing the urine receiver.

Here, the urine receiver described in Japanese Unexamined Patent Application, First Publication No. 2007-44494 includes a urine sensor detecting that urine is excreted. As for the urine sensor, an electrode is formed on a resin film, and the urine sensor includes a portion in which an electrode for electrically connecting with an automatic urine disposing apparatus is exposed. Since a clip which is provided to a tip of a wire connected to the automatic urine disposing apparatus holds between an exposed portion of the electrode, the sensor is electrically connected with the automatic urine disposing apparatus.

DISCLOSURE OF THE INVENTION

Problems to be Solved by the Invention

The terminal portion of the sensor with which the clip is connected is provided so as to be protruded externally in a longitudinal direction from the urine receiver. The terminal portion of the sensor needs to be exposed in order to be connected with the clip. However, the terminal portion of the sensor is formed to be sheet-shaped and thus its strength is low. Therefore, there can be a problem that an exposed portion of the sensor tends to be broken (for example, a portion in which a terminal portion is exposed is rubbed to be broken) during manufacturing process, packaging and conveyance.

The present invention has an object to provide an absorbent article which a terminal portion of a sensor is hard to be broken during manufacturing process, packaging and conveyance.

Means for Solving the Problems

In a first aspect of the present invention, an absorbent article having an elongated shape and disposed so as to cover an excretion portion of a wearer is provided, including: a top sheet portion which is at least partially liquid permeable; a liquid impermeable back sheet portion; and an elongated sensor member capable of detecting liquid excreted from the excretion portion being disposed between the top sheet portion and the back sheet portion along a longitudinal direction of the absorbent article, in which a terminal portion is formed at one end in the longitudinal direction of the sensor member, the terminal portion is covered with the top sheet portion and the back sheet portion when in a first mode, and the terminal portion is uncovered with the top sheet portion and the back sheet portion being exposed externally when in a second mode.

In a second aspect of the present invention, the absorbent article according to the first aspect is provided, including: a joined portion formed at an outer edge of the absorbent article to join the top sheet portion with the back sheet portion; and an unjoined portion formed in a region including the one end in the longitudinal direction of the outer edge, so as not to join the top sheet with the back sheet, in which in the first mode, the top sheet portion and the back sheet portion of the unjoined portion are each laminated, the terminal portion being covered with the top sheet portion and the back sheet portion, and in the second mode, the top sheet portion and the back sheet portion of the unjoined portion are spaced apart from each other, the terminal portion being uncovered with the top sheet portion and the back sheet portion exposed externally.

In the third aspect of the present invention, the absorbent article according to the second aspect is provided, further including: a temporary tacking portion formed on the unjoined portion to allow the top sheet portion and the back sheet portion to be temporarily tacked so as be spaced apart from each other.

In the fourth aspect of the present invention, the absorbent article according to the first aspect is provided, including: a first member; and a second member which is laminated on the first member, the second member including the terminal portion slidable in the longitudinal direction by being laminated on the first member, in which the second member is disposed on the inside of an outer edge of the absorbent article, the terminal portion being covered with the top sheet portion and the back sheet portion when in a first mode, and the second member is slid externally in the longitudinal direction, the terminal portion being uncovered with the top sheet portion and the back sheet portion exposed externally when in a second mode.

In the fifth aspect of the present invention, the absorbent article according the first aspect is provided, in which on the top sheet portion and the back sheet portion of one end in the longitudinal direction of the absorbent article, a plurality of cut-out portions are formed intermittently, so as to be extended in a width direction of the absorbent article, and an end region from the plurality of cut-out portions on the top sheet portion and the back sheet portion to the one end can be separated from the absorbent article, and in which in the first mode, the top sheet portion and the back portion are each laminated, the terminal portion being covered with the top sheet portion and the back sheet portion, and in the second mode, the end region is separated from the absorbent article, the terminal portion being uncovered with the top sheet portion and the back sheet portion and exposed externally.

In the sixth aspect of the present invention, the absorbent article according to the fifth aspect is provided, in which on the other end in the longitudinal direction of the plurality of cut-out portions, a plurality of other cut-out portions is formed in parallel with the plurality of cut-out portions, and a region between the plurality of the other cut-out portions and the plurality of cut-out portions can be separated from the absorbent article.

In the seventh aspect of the present invention, the absorbent article according to the fifth or sixth aspect is provided, in which the plurality of the other portions is formed in a high stiffness region having a greater stiffness than an average stiffness of the top sheet portion and the back sheet portion, respectively.

In the eighth aspect of the present invention, the absorbent article according to the first aspect is provided, including: a joined portion which is formed at an outer edge of the absorbent article to join the top sheet portion with the back sheet portion; and an unjoined portion which is formed at a region including the one end in the longitudinal direction of the outer edge, so as not to join the top sheet portion with the back sheet portion, in which in the first mode, the top sheet portion and the back sheet portion are each laminated, the terminal portion being covered with the top sheet portion and the back sheet portion, and in the second mode, the one end of the top sheet portion and the back sheet portion is moved internally in the longitudinal direction, the terminal portion being uncovered with the top sheet portion and the back sheet portion and exposed externally.

In the ninth aspect of the present invention, the absorbent article according to any one of the first to the eighth aspects is provided, including: an indicator marker indicating a manipulation mode for changing from the first mode to the second mode on the one end of at least one sheet selected from the top sheet portion and the back sheet portion. Effects of the Invention According the present invention, an absorbent article which a terminal portion of a sensor is hard to be broken during manufacturing process, packaging and conveyance can be provided.

BRIEF DESCRIPTION OF THE DRAWINGS

FIG. 1 is a schematic configuration of a system using a urine pad in the first embodiment of the present invention;

FIG. 2B is a plain view showing a configuration of the sensor member of the urine pad in the first embodiment of the present invention;

FIG. 3 is a back side view showing a configuration of the urine pad in the first embodiment of the present invention;

FIG. 12A is an enlarged back side view showing a front edge of the urine pad in the sixth embodiment of the present invention; and FIG. 12B is an enlarged back side view showing that the second output terminal portion is exposed at an end of the front edge the urine pad in the sixth embodiment of the present invention.

PREFERRED MODE FOR CARRYING OUT THE INVENTION

Figure 2A:
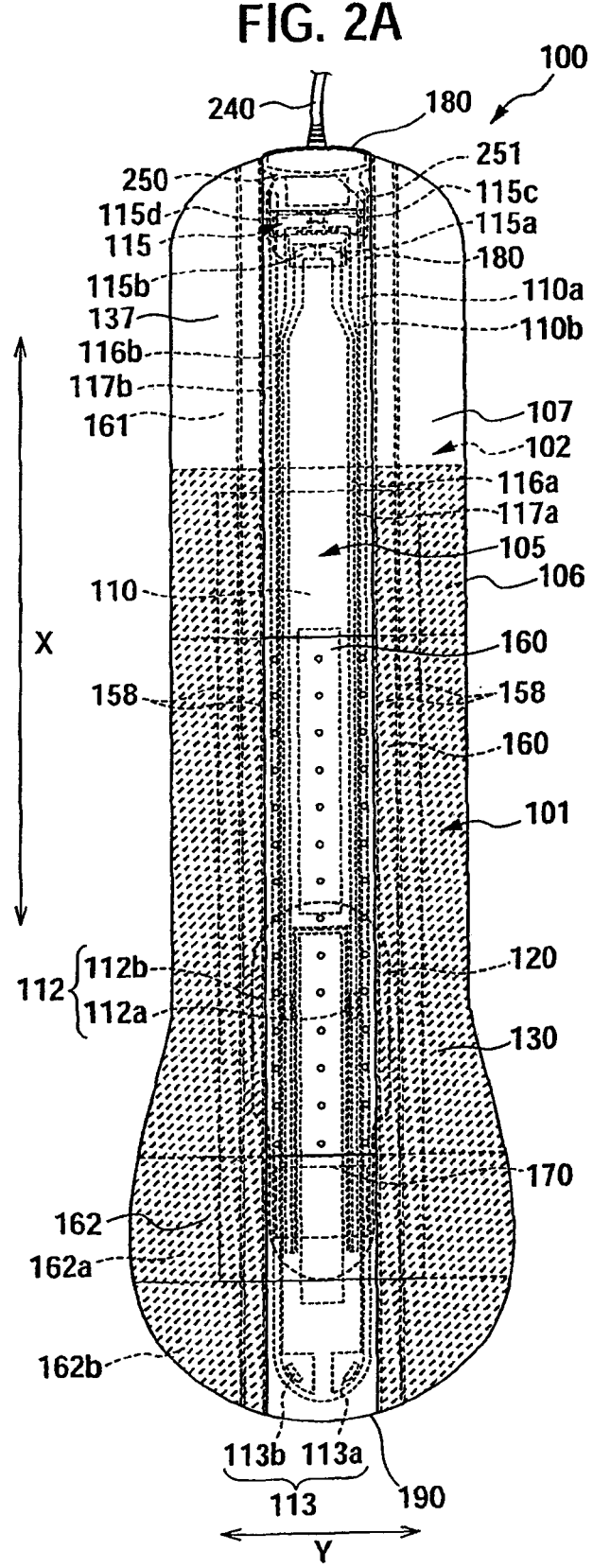
FIG. 2A is a plain view showing a configuration of the urine pad in the first embodiment of the present invention.

1. First Embodiment
1.1 General Description

A urine pad of a first embodiment of the present invention is described with reference to FIGS. 1 to 6. As shown in FIG. 1, a urine pad 100 is used as an absorbent article which is composed of a portion of a system which a device 20 detects liquid such as urine among excretory substances from which a person to which the urine pad 100 is attached excretes and holds the liquid in a container 200 made of resin through a tube 230 using pump 210.

The system 1 is configured with the urine pad 100 and the device 20 including the container 200 and the pump 210. In addition, the device 20 is composed of the container 200, the pump 210, CPU 220, a tube 230, and a wire 240.

The urine pad 100 is connected with the device 20 through the tube 230 and the wire 240. More specifically, the tube 230 connects the container 200 of the device 20 with a collecting portion 120 of the urine pad 100 (described later). Then, the device 20 holds liquid such as urine excreted at the urine pad 100 through the tube 230.

In addition, the wire 240 electrically connects a sensor member 110 (described later) which the urine pad 100 includes with the CPU 220 of the device 20. More specifically, it is connected with the CPU 220 through an input terminal 250 (described later) and the wire 240. The input terminal 250 and the wire 240 are connected with an output terminal portion 115 which is formed as a terminal portion on an end of the sensor member 110. The wire 240 serves as a path transmitting to the CPU 220 a signal such as a detection signal outputted from the output terminal portion 115 of the sensor member 110.

In the present system, the sensor member 110 of the urine pad 100 detects liquid such as urine excreted, and the CPU 220 receives such as a detection signal from the output terminal portion 115 of the sensor member 110 through the input terminal 250 and the wire 240. Then, the CPU 220 actuates the pump 210 of the device 20 and sends liquid such as urine excreted at the urine pad 100 to the container 200 through the tube 230 to hold the liquid in the container 200.

1.2 Urine Pad

The urine pad 100 is a vertically long absorbent article having a first face 101 disposed along a body and a second face 102 disposed opposite the body when a person is wearing the urine pad 100. Here, an absorbent article of the present invention includes an article which absorbs liquid mechanically as well as an article having an absorber with liquid retention capability. More specifically, a urine pad 100 which liquid is taken out to the outside by the device 20 is included in an absorbent article.

As shown in FIG. 1, the urine pad 100 is disposed so as to cover an excretion portion of a wear's body and is attached to the body using an outer member 400 and a band-shaped member 300. More specifically, the extendable band-shape member 300 is disposed circularly along a beltline of a wearer, and an end of the urine pad in a longitudinal direction X is locked with the band-shaped member 300. Then, the outer member 400 is attached to the body so as to cover the excretion portion of a wearer with an end of the urine pad 100 being locked by the band-shaped member 300. Furthermore, the outer member 400 is also attached to the body so as to cover the urine pad 100. As for the outer member 400, for example, underwear such as a diaper attached to a beltline of the wearer can be used.

In addition, as shown in FIG. 2A, the urine pad 100 includes a top sheet portion 105 with liquid permeability disposed on the first face 101, a back sheet portion 106 with liquid impermeability disposed on the second face 102, the sensor member 110 detecting urine and feces, the collecting portion 120 for collecting urines excreted to deliver thereof to the tube 230. On both sides of the top sheet portion 105 in a width direction Y, gathers 158, 158 which are directly contacted with groin are formed, gathers which are deformed to be raised toward a body in the state that the urine pad 100 is attached to the body.

The top sheet portion 105 is composed of a plurality of sheets. More specifically, as shown in FIG. 2A, the top sheet portion 105 is composed of a liquid permeability sheet 160 disposed on the first face 101 of the urine pad 100, a first sheet 161 disposed on a front edge 180, and a second sheet 162 disposed on a back edge 190. The liquid permeability sheet 160 is disposed at a center portion of the urine pad 100 in a width direction Y so as to extend in a longitudinal direction X, and allows liquid such as urine excreted from an excretion portion of a wearer to be permeated. The liquid permeability sheet 160 is not disposed in a vicinity of both ends of the urine pad 100 in a longitudinal direction X. The first sheet 161 and the second sheet 162 (described later) are disposed respectively on both ends of the urine pad 100 in a longitudinal direction X.

Here, the front edge 180 refers to an end disposed on a front side of a body in a case where the urine pad 100 is attached to the body. In addition, the back edge 180 refers to an end disposed on a back side of the body in a case where the urine pad 100 is attached to the body.

The first sheet 161 is composed of a liquid impermeability sheet and disposed so as to cover the output terminal portion 115 of the sensor member 110. On the side of the front edge 180 of the urine pad 100, the first sheet 161 is not joined with the back sheet portion 106. A detailed description of the first sheet 161 and the back sheet portion 106 is made later.

The second sheet 162 has a liquid impermeability portion 162a and a liquid permeability portion 162b. The liquid permeability portion 162b is disposed so as to cover a feces sensor 113. The liquid impermeability portion 162a is disposed on the front edge 180 of the second sheet 162 in order to block liquid such as urine.

As shown in FIG. 3, the back sheet portion 106 is composed of a liquid impermeability sheet and disposed so as to configure the entire second face 102. The back sheet portion 106 prevents liquid such as urine excreted from an excretion portion of a wearer from being permeated, and delivers liquid such as urine to the collecting portion 120 (described later).

Furthermore, on an outer edge of the urine pad 100, a joined portion 130, where the top sheet portion 105 and the back sheet portion 106 are joined each other, is formed in a region except at least a vicinity of an end on the front edge 180. In addition, a region including an end of the front edge 180 is equivalent to an unjoined portion 137 where the top sheet portion 105 and the back sheet portion 106 are not joined each other. More specifically, the joined portion 130 is formed in such a manner that the top sheet portion 105 and the back sheet portion 106 are joined each other at least with more than a half length of the urine pad 100 in a longitudinal direction X from the back edge 190 to the front edge 180. In addition, the sensor member 110 is disposed in the joined portion 130, and a portion except a center region in a width direction Y with which an excretion portion of a body is contacted is joined by hot melt adhesive. More specifically, a shadow area in FIG. 2A is equivalent to the joined portion 130.

As shown in FIG. 2A, the sensor member 110 is disposed at nearly the center of the urine pad 100 in a width direction Y. In addition the sensor member 110 is disposed so as to extend in a longitudinal direction X. The sensor member 110 includes the output terminal portion 115, a urine sensor 112, and the feces sensor 113. The output terminal portion 115 is formed at an end of the front edge 180 of the sensor member 110. The urine sensor 112 is formed between a center portion of the sensor member 110 in a longitudinal direction X and the back edge 190. The feces sensor 113 is disposed at an end of the back edge 190 of the sensor member 110 in a longitudinal direction X.

The sensor member 110 is formed in such a manner that electrically conductive coating is printed on a film 110a which is flexible such as a polyethylene film. More specifically, as shown in FIG. 2B, electrically conductive coating is applied on one face of the film 110a in order to form electrodes 116a, 116b, 117a, and 117b, and a film 110b is laminated so as to cover the electrodes 116a, 116b, 117a, and 117b, thereby forming the sensor member 110.

As shown in FIG. 2B, the output terminal portion 115 includes first connectors 115a and 115b which are electrically connected with the urine sensor 112 and second connectors 115c and 115d which are electrically connected with the feces sensor 113. The film 110b is not disposed in a region where the output terminal portion 115 is formed. That is, in the sensor member 110, the first connectors 115a and 115b, and the second connectors 115c and 115d are exposed outside.

The first connectors 115a and 115b, and the second connectors 115c and 115d thus exposed outside are contacted respectively with each connector (not shown) formed on the input terminal 250 to be electrically connected therewith. Thus, a detection signal and the like outputted from the first connectors 115a and 115b, or the second connectors 115c and 115d are outputted to the CPU 220 via each connector disposed in the input terminal 250.

The urine sensor 112 detects urine in such a manner that first electrodes 112a and 112b are electrically connected with each other by portions of the electrodes 116a and 116b being exposed. More specifically, the urine sensor 112 detects urine in such a manner that the first electrodes 112a and 112b are electrically connected with each other by urine excreted.

Since the first electrodes 112a and 112b are electrically connected with each other by urine excreted, a detection signal as detection result information is outputted from the urine sensor 112. The detection signal is outputted from first connectors 115a and 115b and inputted to the CPU 220 via the input terminal 250 and the wire 240. Since the detection signal is inputted, the CPU actuates the pump 210.

The feces sensor 113 is disposed where urine does not come in and a feces is excreted. In addition, the liquid permeability portion 162b of the second sheet 162 is disposed on an upper face of the feces sensor 113. That is, in a case where a feces is excreted on the liquid permeability portion 162b from an excretion portion of a body, the second electrodes 113a and 113b which are formed by portions of the electrodes 117a and 117b of the feces sensor 113 being exposed are electrically connected with each other by liquid included in a feces, thereby enabling to detect excretion.

Since the electrodes 117a and 117b are electrically connected with each other, a detection signal as detection result information is outputted from the feces sensor 113. The detection signal is outputted from the second connectors 115c and 115d and inputted to the CPU 220 via the input terminal 250 and the wire 240. In a case where a detection signal is inputted, the CPU 220 turns on a light (not shown) which indicates that a feces was excreted.

The collecting portion 120 preferably collects liquid which permeates the liquid permeability sheet 160 of the top sheet portion 105. On a bottom face of the collecting portion 120, a tube connecting portion 121 (see FIG. 3) having a liquid passing path penetrating the bottom face is formed. The tube 230 is connected with the tube connecting portion 121 in such a manner that liquid can be passed therein. Then, the pump 210 indirectly connected with the tube 230 is actuated, and urine collected by the collecting portion 120 is aspirated in the container 200.

1.3 Configuration of Front Edge

Figure 4A:
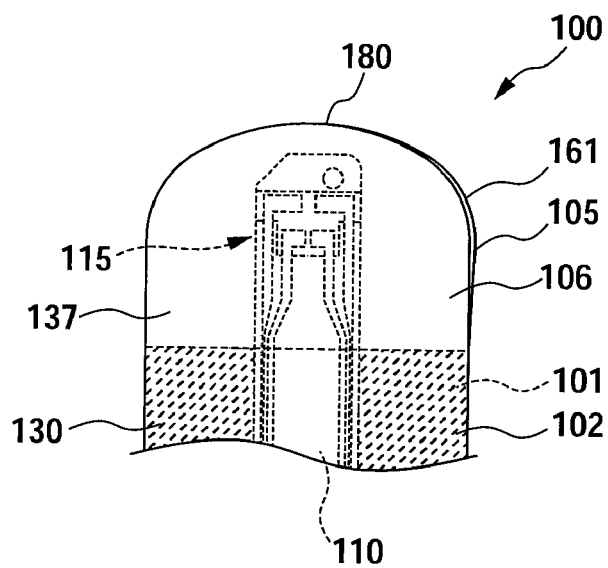
FIG. 4A is an enlarged front view showing a front edge of the urine pad in the first embodiment of the present invention.
Figure 4B:
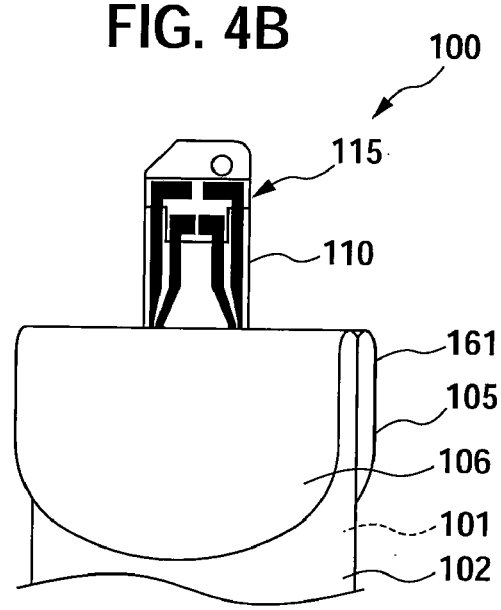
FIG. 4B is an enlarged front view showing that the output terminal portion is exposed at an end of the front edge of the urine pad in the first embodiment of the present invention.
Figure 5:
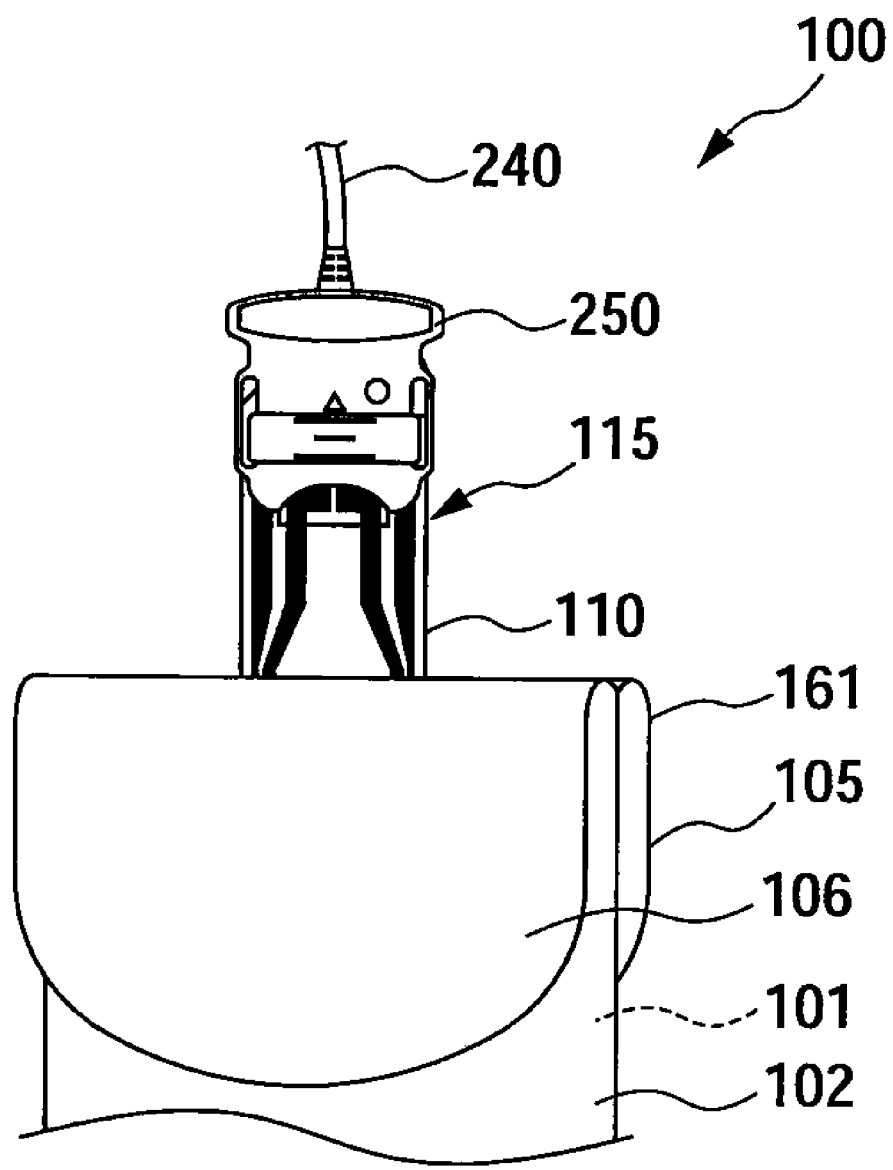
FIG. 5 is an enlarged back side view showing that the output terminal portion is connected with the input terminal on the front edge of the urine pad in the first embodiment of the present invention.

As shown in FIGS. 4A, 4B and 5, the output terminal portion 115 of the sensor member 110 is disposed on the front edge 180 of the urine pad 100. Then, the top sheet portion 105 and the back sheet portion 106 are laminated to be able to be spaced apart from each other so as to cover the output terminal portion 115. That is, the output terminal portion 115 when it is not in use (a first mode) is covered by the top sheet portion 105 and the back sheet portion 106. On the other hand, the output terminal portion 115 when it is in use (a second mode) is exposed.

More specifically, the sensor member 110 is formed in such a manner that its length is nearly the same length or little shorter than that of the top sheet portion 105 or the back sheet portion 106 in a longitudinal direction X. Then, the sensor member 110 is being covered with the first sheet 161 composing the top sheet portion 105, and the back sheet portion 106.

The first sheet 161 and the back sheet portion 106 have an unjoined portion 137 where these sheets are not joined each other on an end of the front edge 180 of the urine pad 100. As shown in FIG. 4A, the unjoined portion 137 is equivalent to a region where the first sheet 161 (composing the top sheet portion 105) and the back sheet portion 106 are not joined each other on an end of the front edge 180, and can be spaced apart from each other in a thickness direction. The output terminal portion 115 is disposed between the first sheet 161 and the back sheet portion 106, and the first face 101 is covered with the first sheet 161 and the second face 102 is covered with the back sheet portion 106.

Then, in a case where the output terminal portion 115 of the sensor member 110 is connected with the input terminal 250 of the device 20 when the urine pad 100 is in use, as shown in FIG. 4B, an end of the front edge 180 of the first sheet 161 is folded back to the first face 101 and an end of the front edge 180 of the back sheet portion 106 is folded back to the second face 102 so that the output terminal portion 115 is exposed.

As shown in FIG. 5, the exposed output terminal portion 115 is electrically connected with the device 20 via the input terminal 250 which is connected with the wire 240 of the device 20. The input terminal 250 is installed so as to tuck the both first and second faces 101 and 102 in the output terminal portion 115. A connector (not shown) formed on the input terminal 250 is contacted with each connector formed in the output terminal portion 115 thereby electrically connecting with each other.

Figure 6:
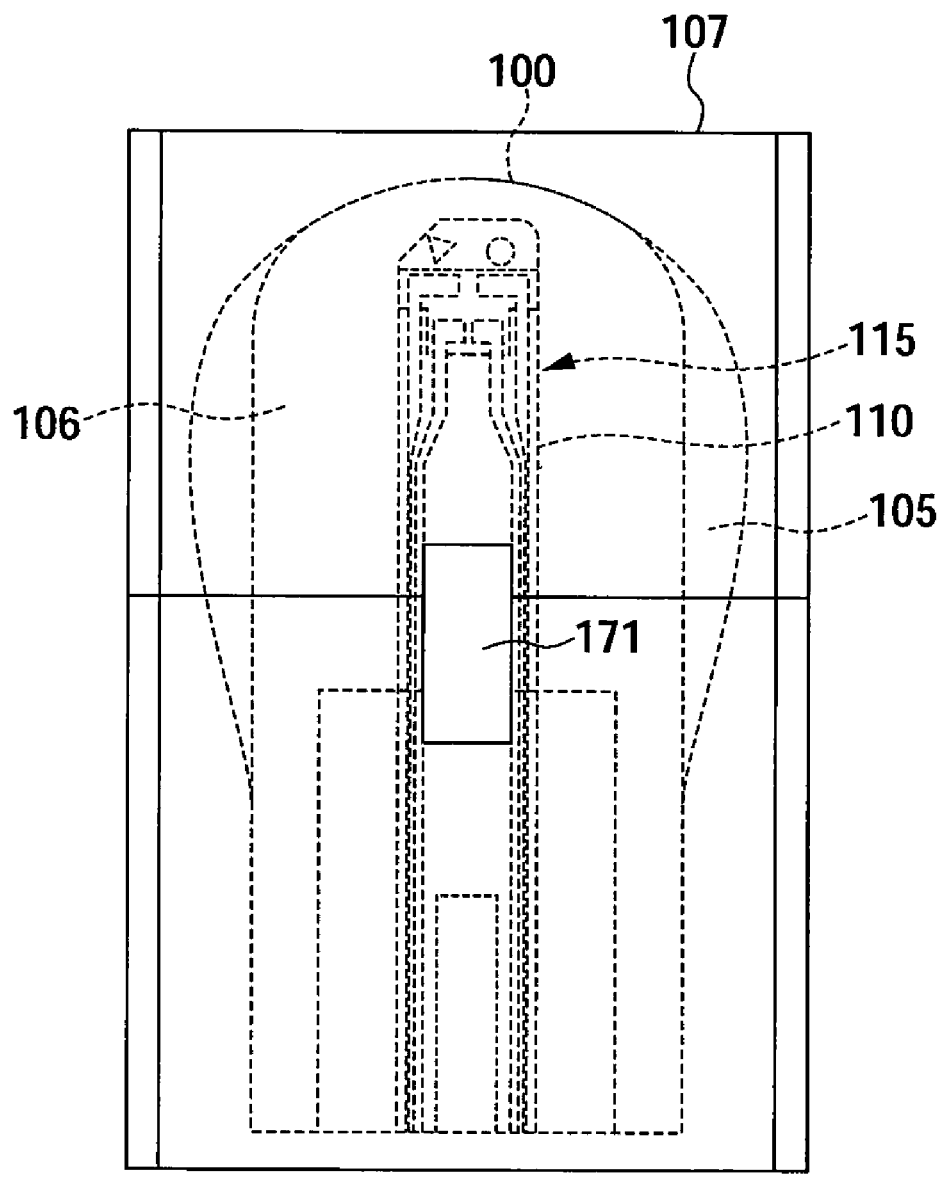
FIG. 6 is a plain view showing a packaging condition of the urine pad in the first embodiment of the present invention.

In addition, as shown in FIG. 6, as a package configuration of the urine pad 100, the urine pad 100 is folded into two at nearly a center portion in a longitudinal direction X and wrapped with a package sheet 107. More specifically, the output terminal portion 115 is wrapped with the package sheet 107 with the output terminal portion 115 being covered with the top sheet portion 105 and the back sheet portion 106. As for the package sheet 107, after the entire urine pad 100 which is folded into two is wrapped, one end is locked with a package tape 171 which is disposed thereat. In addition, a package sheet 107 of the both sides in a longitudinal direction X is joined each other, for example, by hot melt adhesive or embossing, thereby encapsulating the urine pad 100.

In the first embodiment, an indicator marker which indicates a manipulation mode of the top sheet portion 105 and the back sheet portion 106 which are laminated may be provided for changing from not-in-use mode to in-use mode. For example, as described later in a second embodiment, an arrow indicating that the top sheet portion 105 and the back sheet portion 106 can be spaced apart from each other in a thickness direction can be used. Furthermore, an indicator marker is not limited thereof, and may be a dot, a character indicating a manipulation, and the like.

According to the first embodiment, when the urine pad 100 is not in use (the first mode), the output terminal portion 115 is covered with the top sheet portion 105 and the back sheet portion 106. Thus, the output terminal portion 115 is not exposed during manufacturing process, packaging and conveyance. Therefore, it can prevent the first connector and the second connector of which electrodes are exposed at the output terminal portion 115 from being damaged or can prevent the sensor member 110 from being damaged to be broken.

According to the first embodiment, when the urine pad 100 is not in use, the output terminal portion 115 is covered with the first sheet 161 and the back sheet portion 106. On the other hand, in the second mode, when the urine pad 100 is in use, the output terminal portion 115 is exposed. More specifically, the first sheet 161 and the back sheet portion 106 are not joined each other at an end of the front edge 180 and can be spaced apart from each other in a thickness direction, whereby the output terminal portion 114 can be exposed by a simple manipulation. Thus, the output terminal portion 115 can be connected with the input terminal 250 of the device 20.

2. The Other Embodiments

The other embodiments are described with reference to FIGS. 6 to 12B. In the second embodiment to the fifth embodiment, a mode of the top sheet portion 105 and the back sheet portion 106 on the front edge 180 of the urine pad 100 is different. In the sixth embodiment, a mode of the output terminal portion 115, and the top sheet portion 105 and the back sheet portion 106 are different. In the following, the differences from the urine pad 100 in the first embodiment are mainly described. In addition, the following embodiments, unless otherwise noted, are similar to the first embodiment, and the same reference numerals have been retained for similar parts.

2.1 Second Embodiment

Figure 7:
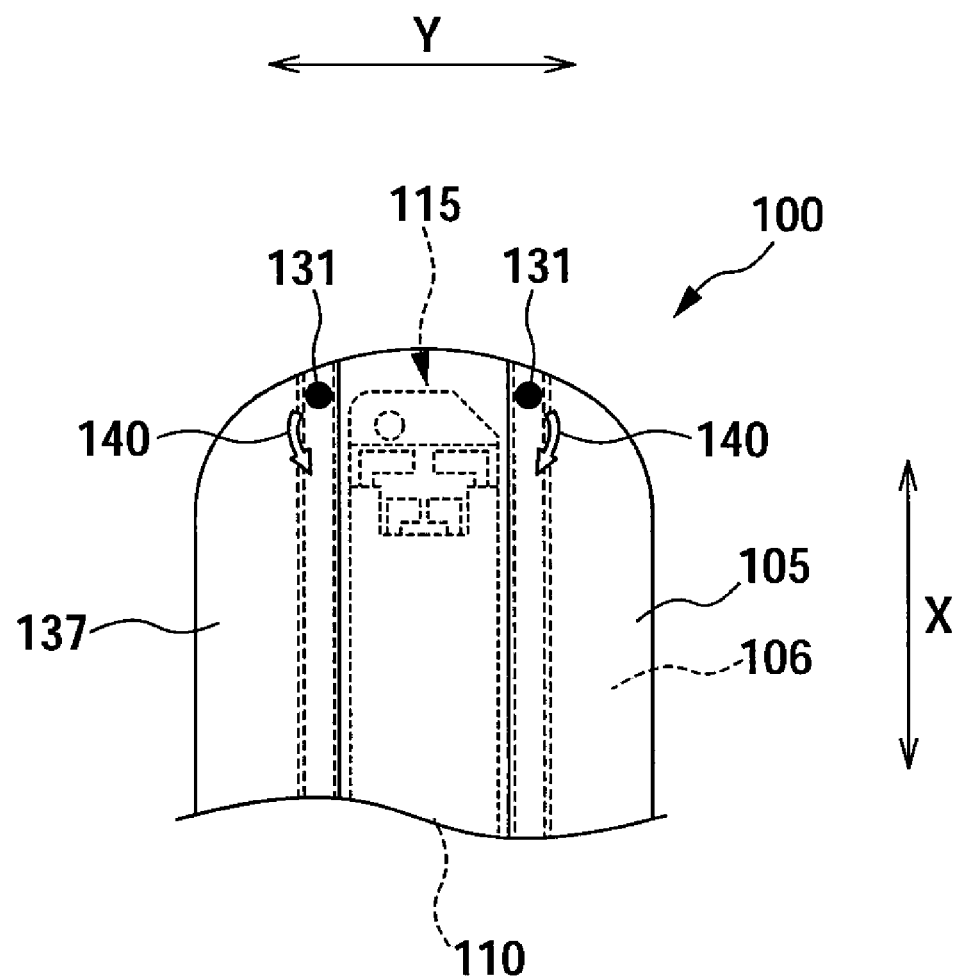
FIG. 7 is an enlarged front view showing a front edge of the urine pad in the second embodiment of the present invention.

As shown in FIG. 7, in the urine pad 100 in the present embodiment, the top sheet portion 105 and the back sheet portion 106 are being temporarily tacked at the unjoined portion 137 by a temporary tacking portion 131. More specifically, the front edge 180 of the top sheet portion 105 and the back sheet portion 106 is not joined each other by the joined portion 130 and is maintained to be spaced apart from each other with a prescribed force by means of the temporary tacking portion 131.

The each temporary tacking portion 131 is formed in a vicinity of both sides in a width direction Y, where the output terminal portion 115 of the top sheet portion 105 and the back sheet portion 106 are disposed therebetween. In other words, the temporary tacking portion 131 is formed at a region in a vicinity of both sides in a width direction Y of the sensor member 110.

In addition, a joint force at the temporary tacking portion 131 which joins the top sheet portion 105 with the back sheet portion 106 is formed to be decreased comparing with a joint force at the joined portion 130. More specifically, the temporary tacking portion 131 is joined by pressure bonding through embossing at a portion of a region on both sides of the sensor member 110 in a width direction Y. Then, when the urine pad 100 is in use, by allowing the top sheet portion 105 and the back sheet portion 106 to be spaced apart from each other respectively in a thickness direction, the temporary tacking portion 131 is released.

By releasing the temporary tacking portion 131, the top sheet portion 105 and the back sheet portion 106 can be spaced apart from each other in a thickness direction, whereby the output terminal portion 115 can be exposed as shown in FIG. 4B.

In addition, as shown in FIG. 7, indication marks 140 as indicator markers may be formed for indicating a manipulation manner during a wearing process. More specifically, an arrow indicating that the top sheet portion 105 is raised in a thickness direction so that the temporary tacking portion 131 is released can be formed. The indication marks 140 can be formed by printing on the top sheet portion 105. In addition, the indication marks can be formed on the back sheet portion 106.

In addition, the indication marks may serve as the temporary tacking portion 131. More specifically, embossing with an arrow shape allows the top sheet portion 105 and the back sheet portion 106 to be joined by pressure bonding. Thus, an arrow-shape temporary tacking portion 131 is formed, and simultaneously it serves as the indication mark 140. In addition, a shape of the indication mark 140 is not limited thereto, and may be any shape which a user can recognize a manipulation manner. For example, a shape may be a dot, a flower petal, a triangle, and the like.

As shown in the second embodiment which includes the temporary tacking portion 131, when a wearer uses the urine pad 100, the output terminal portion 115 can be covered until just before the output terminal portion 115 is connected with the input terminal 250. In addition, the top sheet portion 105 and the back sheet portion 106 are not spaced apart from each other until the output terminal portion 115 is exposed. Accordingly, during a wearing process of the urine pad 100, it can prevent the top sheet portion 105 and the back sheet portion 106 which are spaced apart from each other from interfering a manipulation.

2.2 Third Embodiment

The urine pad 100 in the third embodiment is described with reference to FIGS. 8A and 8B. The urine pad 100 in the third embodiment is different from the first embodiment in that the top sheet portion 105 and the back sheet portion 106 are joined each other at a prescribed portion of the front edge 180.

In the third embodiment, in the urine pad 100, second joined portions 132 are formed in such a manner that the top sheet portion 105 and the back sheet portion 106 are joined each other with these sheets being laminated on both sides of the front edge 180 in a width direction Y.

Figure 8A:
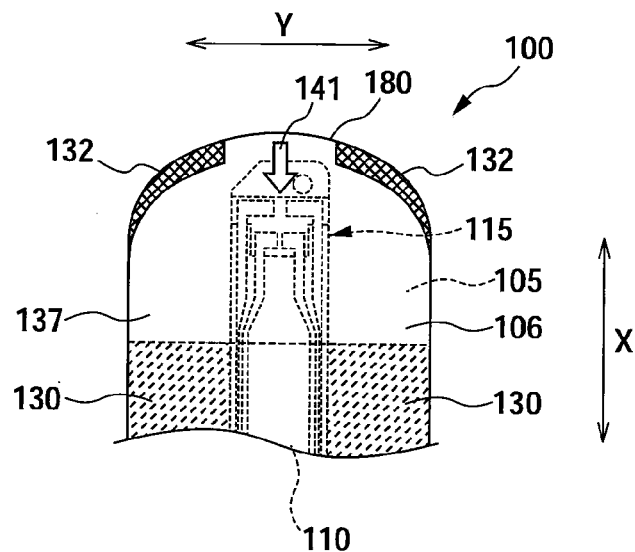
FIG. 8A is an enlarged back side view showing a front edge of the urine pad in the third embodiment of the present invention.
Figure 8B:
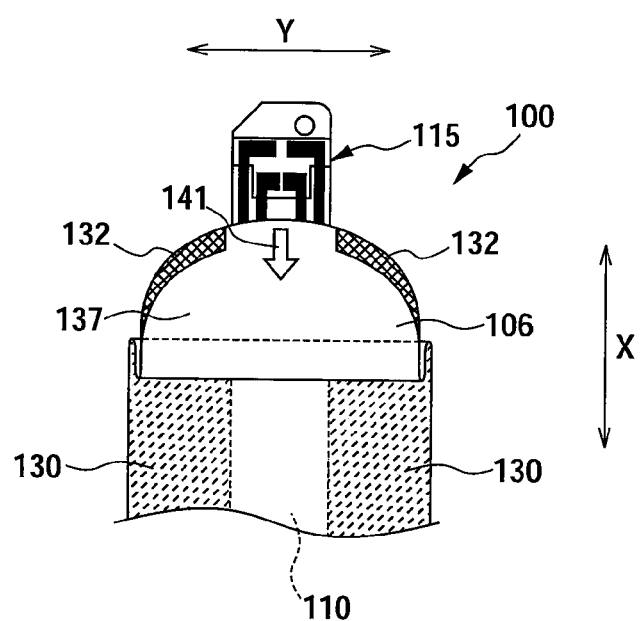
FIG. 8B is an enlarged back side view showing that the output terminal portion is exposed at an end of the front edge of the urine pad in the third embodiment of the present invention.

As shown in FIGS. 8A and 8B, the second joined portions 132 are not connected with the joined portion 130. That is, an unjoined portion 137 is formed between the joined portion 130 and the second joined portions 132, where the top sheet portion 105 and the back sheet portion 106 are not joined each other. That is, at the center portion of the front edge 180 in a width direction Y where one end of an outer edge of the urine pad 100 in a longitudinal direction X is included, the top sheet portion 105 and the back sheet portion 106 are not joined each other. The unjoined portion 137 is equivalent to a region in which the top sheet portion 105 and the back sheet portion 106 are not joined each other. In addition, a width at the center portion of the unjoined portion 137 in a width direction Y at the end of the front edge 180 on the outer edge is broader than a width of the sensor member 110.

When the urine pad 100 is not in use, the top sheet portion 105 and the back sheet portion 106 are being each laminated, and the input terminal 115 of the sensor member 110 is being covered with the top sheet portion 105 and the back sheet portion 106.

When the urine pad 100 is in use, as shown in FIG. 8B, the output terminal portion 115 of the sensor member 110 is exposed. More specifically, an end of the front edge 180 of the top sheet portion 105 and the back sheet portion 106 is moved inwardly (toward the back edge 190) along the sensor member 110 in a longitudinal direction X with the end of the front edge 180 maintaining to be joined by the second joined portion 132. Thus, the output terminal portion 115 is uncovered with the top sheet portion 105 and the back sheet portion 106 and exposed outside.

Since the unjoined portion 137 in which the top sheet portion 105 and the back sheet portion 106 are not joined each other is formed between the joined portion 130 and the second joined portion 132, the top sheet portion 105 and the back sheet portion 106 of an end of the front edge 180 are moved smoothly toward the back edge 190. More specifically, the top sheet portion 105 and the back sheet portion 106 at the unjoined portion 137 where the top sheet portion 105 and the back sheet portion 106 are not joined each other are folded so as to be projected in nearly a convexed shape to the direction to which the sheets are spaced apart from each other in a thickness direction, as the ends of the top sheet portion 105 and the back sheet portion 106 are moved. Thus, the top sheet portion 105 and the back sheet portion 106 can be moved smoothly.

In addition, as shown in FIGS. 8A and 8B, an indication mark 141 as an indicator marker which indicates a direction of moving the end of the front edge 180 may be formed at the top sheet portion 105 and/or the back sheet portion 106. This can easily guides a user how to wear the urine pad.

According to the second embodiment, since the top sheet portion 105 and the back sheet portion 106 are joined each other at both sides of the front edge 180 in a width direction, it can prevent from interfering a manipulation of wearing the urine pad 100, thus enabling to cover the output terminal portion 115 and to expose the output terminal portion 115 when it is in use. Thus, the output terminal portion 115 can be protected until just before it is in use.

2.3 Fourth Embodiment

Figure 9A:
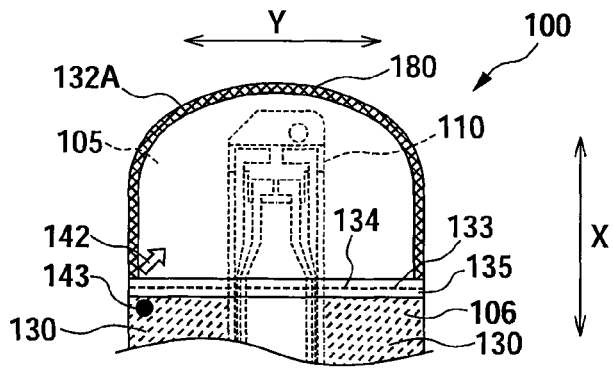
FIG. 9A is an enlarged back side view showing a front edge of the urine pad in the fourth embodiment of the present invention.
Figure 9B:
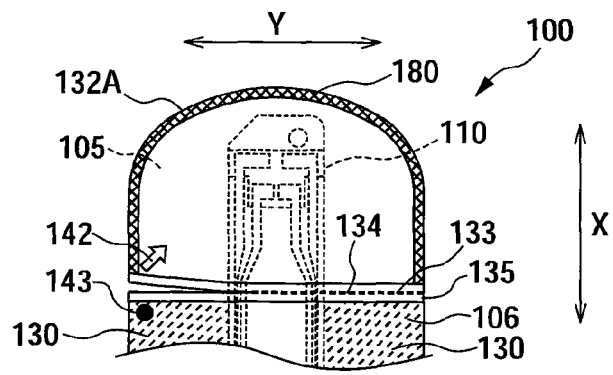
FIG. 9B is a diagram showing that an end of the front edge of the urine pad in the fourth embodiment of the present invention is removed at the cutoff line.
Figure 9C:
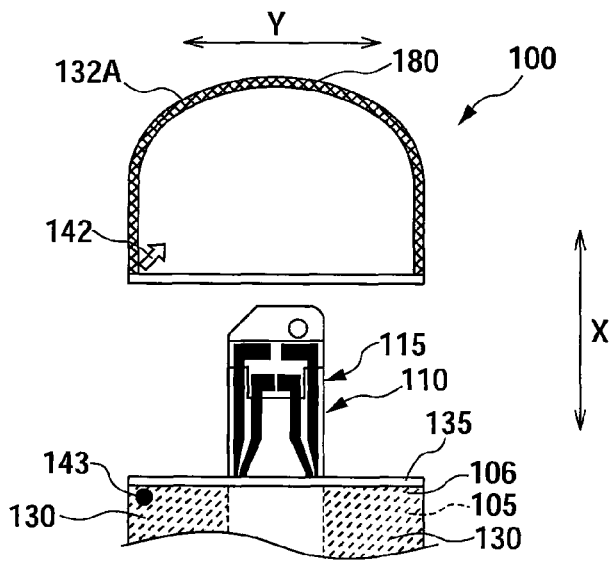
FIG. 9C is an enlarged back side view showing that the output terminal portion is exposed at an end of the front edge of the urine pad in the fourth embodiment of the present invention.

The fourth embodiment is described with reference to FIGS. 9A, 9B, and 9C. In the fourth embodiment, the second joined portion 132A is formed at the entire outer edge of the urine pad 100. Then, at a prescribed location from an end of the front edge 180 toward the back edge 190, a plurality of cut-out portions 134 which extends to the entire width in a width direction Y is formed intermittently, which forms a cutoff line 133. Then, a region from the cutoff line 133 to an end of the front edge 180 is detachable from the urine pad 100.

In addition, the top sheet portion 105 and the back sheet portion 106 are being each laminated, and these sheets are not joined each other except the outer edge. Then, the output terminal portion 115 is disposed so as to be located closer to the front edge 180 than the cutoff line 133. That is, when the urine pad is in use, the output terminal portion 115 of the sensor member 110 is being each laminated, and the top sheet portion 105 and the back sheet portion 106 which are not joined each other are being covered.

The cutoff line 133 is formed to extend in a width direction Y on the top sheet portion 105 and the back sheet portion 106. More specifically, the cutoff line 133 is formed at a prescribed location of the front edge 180 of the urine pad 100 in a longitudinal direction X in such a manner that the cut-out portion 134 is formed intermittently so as to extend in a width direction Y.

When the urine pad is in use, an end of the front edge 180 of the top sheet portion 105 and the back sheet portion 106 is removed along the cutoff line 133 from one end to the other end of the cutoff line 133 in a width direction Y, whereby the output terminal portion 115 is exposed. More specifically, in FIGS. 9B and 9C, one end of the cutoff line 133 in a width direction Y is gripped so that an end of the front edge 180 of the top sheet portion 105 and the back sheet portion 106 is pulled toward the front edge 180. Thus, the end of the front edge 180 of the top sheet portion 105 and the back sheet portion 106 where the cut-out portion 134 is connected continuously is removed.

It is preferred that a stiffness in a proximal region 135 formed along the cutoff line 133 is higher than average stiffness in the other regions of the top sheet portion 105 and the back sheet portion 106. Because of its high stiffness, the region 135 serves as a guide when the end of the front edge 180 is removed along the cutoff line 133, and it can prevent a region other than the cutoff line 133 from being broken.

In addition, on either end of the cutoff line 133, indication marks 142 and 143 as indicator markers which indicate a manipulation mode of the top sheet portion 105 and/or the back sheet portion 106 may be provided for changing from not-in-use mode to in-use mode. For example, an indication mark 142 such as an arrow indicating a direction to pull an end of the front edge is formed on a side which is removed along the cutoff line 133. In addition, on a side which is not removed along the cutoff line 133, an indication mark 143 such as a dot, a square, and the like, which indicating a gripping position, is formed. In addition, shapes of the indication marks 142 and 143 are not limited thereto. This can easily guides a user how to wear the urine pad.

In fourth embodiment, although the cutoff line 133 is formed on the top sheet portion 105 and the back sheet portion 106, the cutoff line 133 may be formed on either one of the top sheet portion 105 and the back sheet portion 106. In this case, the output terminal portion 115 is exposed in such a manner that, after either one of the top sheet portion 105 and the back sheet portion 106 is removed along the cutoff line 133, the other sheet which was not removed is folded back.

In the fourth embodiment, since the output terminal portion 115 of the sensor member 110 is covered with the top sheet portion 105 and the back sheet portion 106 when the urine pad is not in use, it can prevent the output terminal portion 115 from being broken during manufacturing process, packaging and conveyance.

In the present embodiment, since an end of the front edge 180 can be removed along the cutoff line 133 on the top sheet portion 105 and the back sheet portion 106, it can prevent a portion which covers the output terminal portion 115 when the urine pad is in use from interfering a wearer's movement.

2.4 Fifth Embodiment

Figure 10A:
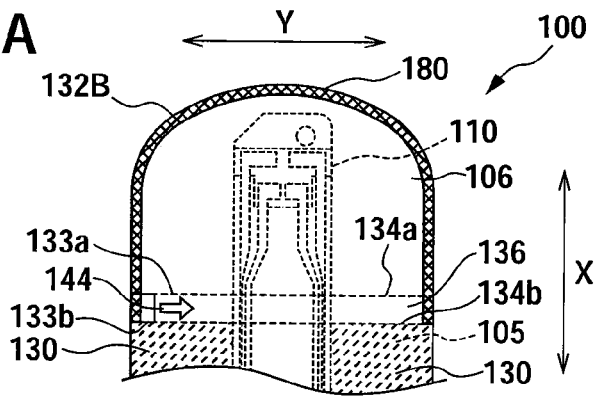
FIG. 10A is an enlarged back side view showing a front edge of the urine pad in the fifth embodiment of the present invention.
Figure 10B:
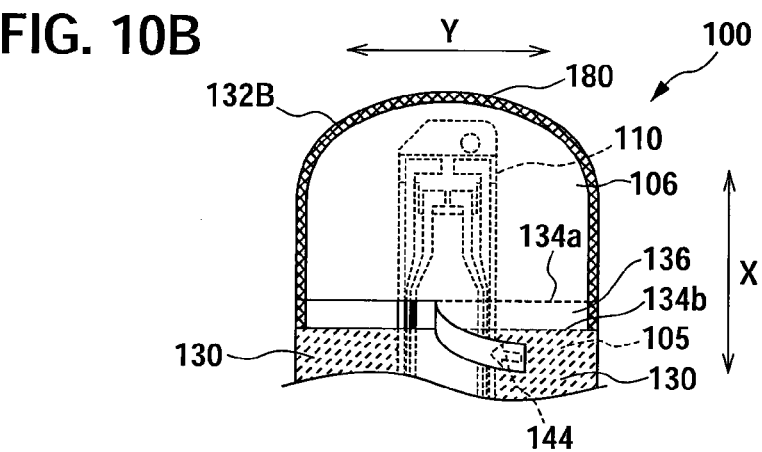
FIG. 10B is a diagram showing that an end of the front edge of the urine pad in the fifth embodiment of the present invention is removed by the cut-out portion.

The fifth embodiment is described with reference to FIGS. 10A and 10B. Regarding the urine pad 100 of the fifth embodiment, the second joined portion 132B is formed at the entire outer edge of the urine pad 100. Then, at a prescribed location from an end of the front edge 180 toward the back edge 190, a cut-out portion 136 is formed so as to extend in a width direction Y.

A cut-out portion 136 is formed so as to extend in a width direction Y at a prescribed location from an end of the front edge 180. In addition, the cut-out portion 136 is a region between a cutoff line 133a and a cutoff line 133b. The cutoff line 133a is formed by forming intermittently a plurality of cut-out portion 134 so as to be extended in a width direction Y. The cutoff line 133b is formed by forming the other cut-out portion 134b which is formed to be nearly parallel. The cutoff lines 133a and 133b is formed on the top sheet portion 105 and the back sheet portion 106. Therefore, the cut-out portion 136 sandwiched between the cutoff lines 133a and 133b is formed so as to make a circuit of the urine pad 100 in a width direction Y. At the region closer to the front edge 180 than the cutoff line 133b, the top sheet portion 105 and the back sheet portion 106 are not joined each other except an outer edge. Then, the output terminal portion 115 is disposed so as to be located closer to the front edge 180 than the cutoff line 133b.

When the urine pad is not in use, the output terminal portion 115 of the sensor member 110 is being covered with the top sheet portion 105 and the back sheet portion 106 which are laminated. On the other hand, when the urine pad is in use, by pulling one end of the cut-out portion 136 in a width direction Y toward the other end, the cut-out portion 136 is removed along the cutoff lines 133a and 133b.

Thus, a region from the cut-out portion 136 to an end of the front edge 180 is separated from the urine pad 100. Then, the output terminal portion 115 of the sensor member 110 is exposed.

At one end of the cut-out portion 136 in a width direction Y, an indication mark 143 as an indicator marker which indicates a manipulation mode may be provided for changing from not-in-use mode to in-use mode. The indication mark 144 is similar to the indication mark 140 in the second embodiment. The indication mark 144 is formed, and this can easily guides a user how to wear the urine pad.

Figure 10C:
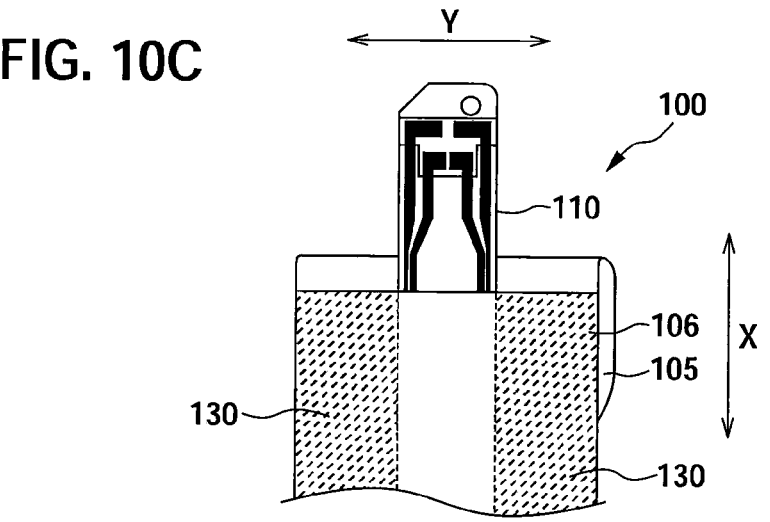
FIG. 10C is an enlarged back side view showing that the output terminal portion is exposed at an end of the front edge of the urine pad in the fifth embodiment of the present invention.

In addition, the cut-out portion 136 may not be formed on the both the top sheet portion 105 and the back sheet portion 106 and may be formed on either sheet. In this case, an end of the front edge 180 of a sheet on which the cut-out portion 136 is not formed is not removed. Therefore, the sensor member 110 is exposed in such a manner that it is pulled from an opening which is formed after the cut-out portion 136 is removed. In addition, as shown in FIG. 10C, a sheet which was not removed is folded back externally in a thickness direction of the urine pad 100.

In the fifth embodiment, since the output terminal portion 115 of the sensor member 110 is covered with the top sheet portion 105 and the back sheet portion 106 when the urine pad is not in use, it can prevent the output terminal portion 115 from being broken during manufacturing process, packaging and conveyance. In addition, by removing the cut-out portion 136, the output terminal portion 115 of the sensor member 110 can be easily changed from a covered mode to an exposed mode.

2.5 Sixth Embodiment

The sixth embodiment is described with reference to FIGS. 11A, 11B, 12A, and 12B. In the sixth embodiment, a second sensor member 500 as a second member is slidably laminated at an end of the front edge of the sensor member 110 as a first member. In addition, a second joined portion 132C is formed along an outer edge except an outer edge of the front edge 180 where the sensor member 110 and the second sensor member 500 are disposed.

The length of the second sensor member 500 is formed to be shorter than that of the sensor member 110 in a longitudinal direction X. In addition, protrusions 510a re formed so as to be protruded externally in a width direction Y at an end of the back edge 190 of the second sensor member 500.

Figure 11A:
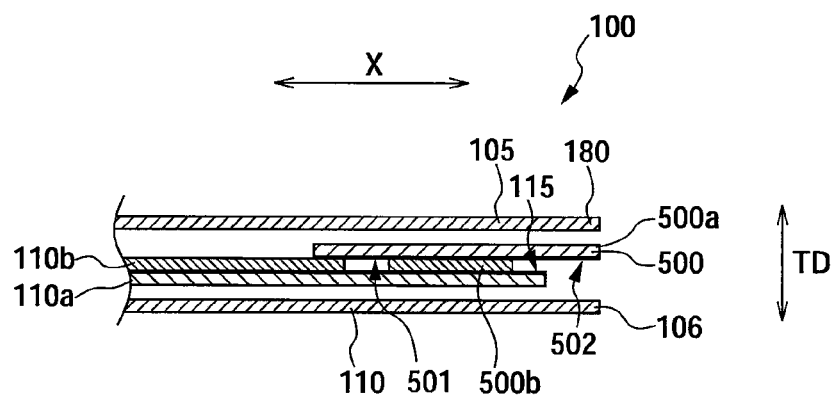
FIG. 11A is an enlarged sectional view showing that the front edge of the urine pad in the sixth embodiment of the present invention is cut off in a longitudinal direction.
Figure 11B:
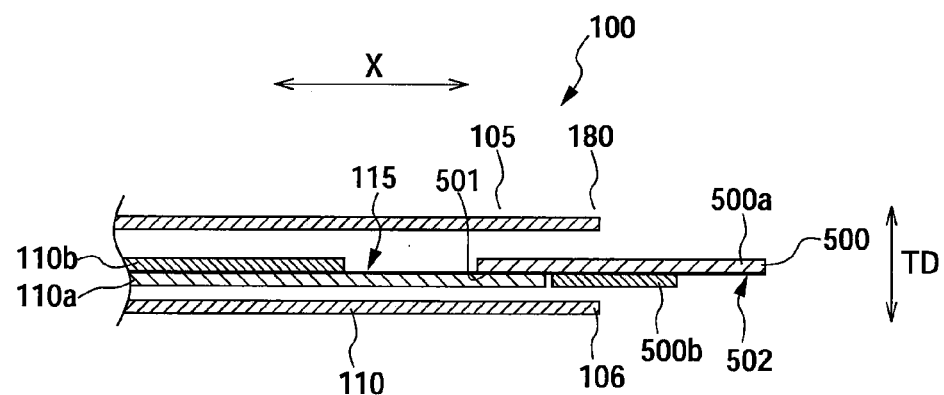
FIG. 11B is an enlarged sectional view showing that the front edge of the urine pad in the sixth embodiment of the present invention is cut off in a longitudinal direction.

As shown in FIGS. 11A and 11B, the second sensor member 500 is laminated on the top sheet portion 105 of the sensor member 110. Then, the second input terminal portion 501 is formed on a contact surface of the second sensor member 500 with the sensor member 110, and a second input terminal portion 501 is contacted with the input terminal portion 115 of the sensor member 110, thereby electrically connecting with each other.

In addition, the second output terminal portion 502 is formed on an end of the front edge 180 of the second sensor member 500. Then, the abovementioned input terminal 250 is connected with the second output terminal portion 502. In the sixth embodiment, as shown in FIGS. 11A and 11B, the second output terminal portion 502 is formed at a contact surface with the sensor member 110 of the second sensor member 500.

Similar to the sensor member 110, the second sensor member 500 is formed in such a manner that electrically conductive coating is printed on a film 500a which is flexible such as a polyethylene film. More specifically, electrically conductive coating is applied on one face of the film 500a in order to form an electrode, and a film 500b is laminated so as to cover the electrode thus formed. Then, the second input terminal portion 501 is formed on the front edge 190 of the second sensor member 500. At the second input terminal portion 501, conductive parts (not shown) are formed by exposing an electrode, and are formed at a position facing first connectors 115a and 115b, and second connectors 115c and 115d of the sensor member 110 respectively, each of which is laminated conductively.

In addition, the second output terminal portion 502 is composed of third connectors 502a and 502b, and fourth connectors 502c and 502d with which the input terminal 250 of the device 20 is connected. The third connectors 502a and 502b output a detection signal and the like from the urine sensor 112 of the sensor member 110 to the input terminal 250. In addition, the fourth connectors 502c and 502d output a detection signal and the like from the feces sensor 113 to the input terminal 250.

The third connectors 502a and 502b, and the fourth connectors 502c and 502d are electrically connected in such a manner that a connector (not shown) in the input terminal 250 is contacted with each connector formed in the second output terminal portion 502.

The second sensor member 500 is slidably laminated on the sensor member 110. When the urine pad 100 is not in use, as shown in FIG. 12A, the second sensor member 500 is being covered with the top sheet portion 105 and the back sheet portion 106. Then, when the urine pad 100 is in use, in a case where the second sensor member 500 is slid to move to the front edge 180, as shown in FIG. 12B, the second output terminal portion 502 is being exposed.

When the second sensor member 500 is moved to an end of the front edge 180, the protrusion 510 is hooked with the second joined portion 132C. Accordingly, the second sensor member 500 cannot move externally in a longitudinal direction X. The second joined portion 132C may be formed so as to be along an outer edge, or may be formed to be a protruded shape so as to be protruded internally in a longitudinal direction X on both sides in a width direction Y at which the sensor member 110 and the second sensor member 500 on the outer edge are disposed. By forming the abovementioned shape, the second joined portion 132C is engaged with the protrusion 510, and serves as a stopper.

In the sixth embodiment, although the output terminal portion 115 of the sensor member 110 is formed at the entire region where the second sensor member 500 is slid in a longitudinal direction X and the second input terminal portion 501 is contacted, the present invention is not limited thereto. For example, in a case where the second sensor member 500 is moved to an outermost edge of the front edge 180, the output terminal portion 115 may be formed only in a region where the input terminal portion 501 of the second sensor member 500 is contacted. That is, only when the second sensor member 500 is moved to the outermost edge of the front edge 180, the sensor member 110 and the second sensor member 500 can be conductive.

In addition, in the sixth embodiment, although the second sensor member 500 is laminated on the sensor member 110, the present invention is not limited thereto. For example, concavity and convexity can be formed alternatively and continuously on an end of front edge 180 of the sensor member 110. That is, by forming the end of the front edge 180 of the sensor member 110 to be an accordion shape, the output terminal portion 115 is covered with the top sheet portion 105 and the back sheet portion 106 with the output terminal portion 115 being compressed most. Then, the sensor member 110 in an accordion shape is made to stretch, thereby enabling to expose the output terminal portion 115. In addition, as well as so-called an accordion shape, the sensor member 110 may be folded back one time in order to form it to be a Z shape.

In the sixth embodiment, since the second output terminal portion 502 of the second sensor member 500 is covered with the top sheet portion 105 and the back sheet portion 106 when the urine pad is not in use, it can prevent the output terminal portion 115 from being broken during manufacturing process, packaging and conveyance. In addition, by pulling the second sensor member 500 externally to the front edge 180, the second input terminal portion 502 can be easily changed from a covered mode to an exposed mode.

Although the second embodiment to the sixth embodiment are described as the other embodiments of the present invention, modes of the top sheet portion 105 and the back sheet portion 106 are not limited thereto. For example, when the urine pad is not in use, the other member which covers the input terminal portion 115 of the sensor member 110 cover the input terminal portion 115, and when the urine pad is in use, the other member may be removed so as to expose the output terminal portion 115. In addition, in the first embodiment, although the top sheet portion 105 and the back sheet portion 106 can be spaced apart from each other in a thickness direction, a cutoff line may be provided at a prescribed location of the unjoined portion 137 so that an end region of the front edge 180 is cut off from the urine pad 100 as described in the third embodiment or the fourth embodiment.

The invention claimed is:

1. An absorbent article having an elongated shape for covering an excretion portion of a wearer, comprising:
    a front face sheet which is at least partially liquid permeable; a liquid impermeable rear face sheet; and
    an elongated sensor member capable of detecting liquid excreted from the excretion portion being disposed between front face sheet and the rear face sheet along a longitudinal direction of the absorbent article,
    wherein a terminal portion is formed at one end in the longitudinal direction of the sensor member, and
    the front face sheet and the rear face sheet extend continuously over opposite surfaces of the elongated sensor and include portions that extend over the terminal portion of the elongate sensor that arc not permanently joined so that the portions that extend over the terminal portion of the sensor can be superposed to cover the terminal portion of the sensor in a first mode or pulled apart to expose the terminal portion of the sensor in a second mode;
    wherein on the front face sheet and the rear face sheet of one end in the longitudinal direction of the absorbent article, a plurality of cut-out portions are formed intermittently, so as to be extended in a width direction of the absorbent article, and
    an end region from the plurality of cut-out portions on the front face sheet and the rear face sheet to the one end can be separated from the absorbent article, and wherein in the first mode, the front face sheet and the rear face sheet are each laminated, the terminal portion being covered with the front face sheet and the rear face sheet, and
    in the second mode, the end region is separated from the absorbent article, the terminal portion being uncovered with the front face sheet and the rear face sheet and exposed externally.

2. The absorbent article according to claim 1,
    wherein on the other end in the longitudinal direction of the plurality of cut-out portions, a plurality of other cut-out portions is formed in parallel with the plurality of cutout portions, and
    a region between the plurality of the other cut-out portions and the plurality of cutout portions can be separated from the absorbent article.

3. The absorbent article according to claim 1, wherein the plurality of the other portions is formed in a high stiffness region having a greater stiffness than an average stiffness of the front face sheet and the rear face sheet, respectively.

4. The absorbent article according to claim 1, comprising:
    an indicator marker indicating a manipulation mode for changing from the first mode to the second mode on the one end of at least one sheet selected from the front face sheet and the rear face sheet.

* * * * *